United States Patent
Qin et al.

(10) Patent No.: US 10,807,937 B2
(45) Date of Patent: Oct. 20, 2020

(54) SOLID-SOLID SEPARATION PROCESS FOR LONG CHAIN DICARBOXYLIC ACIDS

(71) Applicants: CATHAY BIOTECH INC., Shanghai (CN); CIBT AMERICA INC., Newark, DE (US)

(72) Inventors: Bingbing Qin, Shanghai (CN); Yufeng Yang, Shanghai (CN); Xiucai Liu, Shanghai (CN)

(73) Assignees: CATHAY BIOTECH INC., Shanghai (CN); CIBT AMERICA INC., Newark, DE (US)

( * ) Notice: Subject to any disclaimer, the term of this patent is extended or adjusted under 35 U.S.C. 154(b) by 0 days.

(21) Appl. No.: 16/339,756

(22) PCT Filed: Jul. 11, 2016

(86) PCT No.: PCT/CN2016/089615
§ 371 (c)(1),
(2) Date: Apr. 5, 2019

(87) PCT Pub. No.: WO2018/010057
PCT Pub. Date: Jan. 18, 2018

(65) Prior Publication Data
US 2019/0248726 A1 Aug. 15, 2019

(51) Int. Cl.
*C07C 51/43* (2006.01)
*C07C 51/42* (2006.01)
*C07C 55/21* (2006.01)
*C12P 7/64* (2006.01)
*C07C 51/02* (2006.01)
*C07C 51/347* (2006.01)
*C12P 7/44* (2006.01)

(52) U.S. Cl.
CPC .............. *C07C 51/43* (2013.01); *C07C 51/02* (2013.01); *C07C 51/347* (2013.01); *C07C 51/42* (2013.01); *C07C 55/21* (2013.01); *C12P 7/44* (2013.01); *C12P 7/6409* (2013.01)

(58) Field of Classification Search
CPC .. C12P 7/74; C12P 7/64; C12P 7/6409; C12P 7/44; C07C 55/21; C07C 51/43; C07C 51/42; C07C 51/347
See application file for complete search history.

(56) References Cited

U.S. PATENT DOCUMENTS

| | | | | |
|---|---|---|---|---|
| 6,288,275 B1 * | 9/2001 | Turner | ............... | C07C 51/43 435/142 |
| 9,517,996 B2 * | 12/2016 | Laplaza | ............... | C07C 55/20 |
| 2013/0116471 A1 * | 5/2013 | Yan et al. | ............... | C07C 51/43 562/593 |
| 2015/0025259 A1 * | 1/2015 | Yang | ............... | C07C 51/02 554/121 |
| 2015/0361024 A1 | 12/2015 | Laplaza | | |

FOREIGN PATENT DOCUMENTS

| CN | 103570525 A | * | 2/2014 | ............ C07C 51/42 |
|---|---|---|---|---|
| JP | S5615695 A | | 2/1981 | |

OTHER PUBLICATIONS

CN 103570525 (A), Li Xiaoshu et al., Method for refining long-chain dibasic acid, 2014, English translation, 9 pages (Year: 2014).*
English, J. J., et al., The wound hormones of Plants. IV. Structure and Synthesis f a Traumatin, vol. 61, pp. 3434-3436 (Year: 1939).*
Kroha, K., Industrial biotechnolog provides opportunities from commercial production of long chain dibasic acids, 2004, Inform, vol. 15(9), pp. 568-571 (Year: 2004).*
International Search Report and Written Opinion issued in Application No. PCT/CN2016/089615 dated Apr. 10, 2017, 9 pages.
Pu, Weixiao et al., "Treatment of emulsion wastewater with heating and acidification-Fenton oxidation", Chinese Journal of Environmental Engineering, vol. 7, No. 10, Oct. 5, 2013, pp. 4027-4031.
Chen, Chin-Ming et al., "Influence of pH on the stability of oil-in-water emulsions stabilized by a splittable surfactant", Colloids and Surfaces, vol. 170, No. 2-3, Sep. 30, 2000, pp. 173-179.
Communication and Supplementary European Search Report in Europe application No. EP 16908390.4 dated May 11, 2020, 10 pages.

* cited by examiner

*Primary Examiner* — Yate' K Cutliff
(74) *Attorney, Agent, or Firm* — Rothwell, Figg, Ernst & Manbeck, P.C.

(57) ABSTRACT

The present disclosure provides a method for isolating a long chain dicarboxylic acid from fermentation broth containing microbial cells. Also provided is a substantially pure long chain dicarboxylic acid isolated by the method.

22 Claims, No Drawings

SOLID-SOLID SEPARATION PROCESS FOR LONG CHAIN DICARBOXYLIC ACIDS

BACKGROUND OF THE INVENTION

Long chain carboxylic acids are useful for the production of nylons and other polyamides, resins, polyesters, fragrances or perfumes, adhesives, powder coatings, corrosion inhibitors, lubricants, plasticizers, and pharmaceutical products. These carboxylic acids can be generated on an industrial-scale from long-chain n-alkanes and/or fatty acids via fermentation of microbial cells.

The standard method used to separate long chain dicarboxylic acids from a fermentation broth can include: (1) adjusting the pH of the broth to about 8 to about 10 by adding a base to the broth, (2) heating the broth and applying membrane filtration to remove cells and obtain a clear broth containing dibasic acid salts; (3) adding an acid such as sulfuric acid ($H_2SO_4$) to precipitate the dibasic acid; and (4) filtration and drying the precipitated dibasic acid to recover the long chain dicarboxylic acid product.

For instance, Chinese Patent No. CN1053470C describes a method that includes adding an alkali to a fermentation broth containing brassylic acid (DC13) to adjust the pH value at the range of 10-12. The broth is then heated to 85-90° C. and demulsified. In some cases, the upper layer of the residual oil is recycled. The middle layer is collected as a clear broth. The cells layer can be re-treated to obtain a second clear broth or be sent directly for centrifugation or filtration. The clear broth is then decolorized using activated carbon for 30 min at 85-90° C. Thereafter the activated carbon can be removed. The decolored solution is heated to 60-70° C. and either HCl or $H_2SO_4$ is added into the decolored solution to adjust the pH value range to 4-5 for acidification and crystallization to obtain the long chain diacid product.

The pH of the starting fermentation broth is usually about pH 7-8. In this method, a large amount of alkali is used to demulsify the broth and to remove the alkane and cells. For example, the pH of the broth is typically raised to about pH 10-12. After the acidification step, excess alkali is also used to neutralize the corresponding excess acid. As a result, excess salts are produced and discharged into the waste water.

Chinese Patent No. CN97121846.3 describes a method that includes demulsifying a fermentation broth by adding alkali, and then removing the microbial cells by filtration. The broth is then acidified to obtain a crude dicarboxylic acid. Alkali and water are added to the crude acid to dissolve the salt, and recover the salt by a salting-out method. The recovered salt is then dissolved in water and filtered to remove impurities. Next, the filtrate is then acidified to obtain the desired long chain dicarboxylic acid. A key disadvantage of this method is the consumption of large amounts of acids and alkali.

In the separation method described in Chinese Patent Application Publication No. CN103570525A, the residual alkane and microbial cells are separated from the clear broth phase by centrifugation. An alkali solution (about 4 mg/L-400 mg/L alkali solution) is added to the separated cell phase, and then the cells are lysed and separated by membrane filtration. The membrane filtrate is combined with the clear broth phase. Alkali is then added to the mixture to adjust the pH to about 8.0-10.5. This treated mixture then undergoes decoloration, separation and acidification to produce the desired long chain dicarboxylic acid.

The conventional process for extracting dicarboxylic acids from a fermentation broth is (1) to dissolve the acids using an alkali, (2) to remove the cells by filter or membrane filtration or centrifugation, and (3) to acidify the dicarboxylic acid salt. Because of the high viscosity of fermentation broths, it can be difficult to separate cells from the broth by using standard filtering equipment. To solve such problems, a microfiltration membrane can be used. However, membrane filtration equipment is extremely costly and requires a large amount of power to operate. Also, the membrane units typically last for only 2-3 years before expensive servicing is required. In some cases, excess alkali must be added into the fermentation broth to increase the pH value at the range of 8.5-11.0 for full demulsification and proper extraction. To produce the desired dicarboxylic acid, the excess alkali must be neutralized by acidification which in turn can produce a large amount of salt in the wastewater. Also the precipitated the dicarboxylic acids must be separated from the acidified solution by appropriate equipment. Repeating filtering and separating can have adverse effects on the product yield.

For instance, such a demulsifying method is described Chinese Patent No. CN104693018A. The fermentation broth of long chain diacid is directly acidified, and both the precipitated dicarboxylic acid and microbial cells are separated from the broth and collected together. They are then dried. Eventually, the cells are removed in subsequent purification processes that use an organic solution. A key problem with this method is the presence of organic impurities which can be insoluble in an organic solvent. As such, the method leads to a risk of low product purity and high product loss.

Isolating substantially pure or pure dicarboxylic acids from fermentation broths remains a challenge.

BRIEF SUMMARY OF THE INVENTION

In one aspect, described herein is a method for isolating a long chain dicarboxylic acid from a fermentation broth containing microbial cells. The method includes (a) adding an acid to the fermentation broth to produce a demulsified fermentation broth having a pH of 6 or less; (b) centrifuging the demulsified fermentation broth to generate a first phase comprising the long chain dicarboxylic acid and a second phase comprising the microbial cells; and (c) isolating the long chain dicarboxylic acid from the first phase to recover an isolated long chain dicarboxylic acid.

The method can further comprise heating the fermentation broth to a temperature from about 90° C. to about 105° C. prior to step (a). Alternatively, the method can further comprise heating the demulsified fermentation broth to a temperature from about 90° C. to about 105° C. prior to step (b). The method can also comprise cooling the demulsified fermentation broth to a temperature from about 30° C. to about 80° C. after heating (e.g., heating prior to step (a) and heating prior to step (b)).

In some embodiments, the first phase is substantially free of the microbial cells. The second phase can be substantially free of the long chain dicarboxylic acid. In some instances, the fermentation broth is a sterilized fermentation broth.

In some embodiments, the acid is selected from the group consisting of sulfuric acid, hydrochloric acid, nitric acid, acetic acid, phosphoric acid, trifluoromethane sulfonic acid, and any combination thereof. In some instances, the acid is sulfuric acid. In some cases, the demulsified fermentation broth has a pH of 2-5. In other cases, the pH is from pH 2.5-4. In some embodiments, the demulsified fermentation broth has a viscosity of about 5 centipoise (cp)-about 200 cp.

Centrifuging can comprise sequential centrifugation. In some instances, centrifuging is performed using a scanter centrifuge. The scanter centrifuge can be selected from the group consisting of a hydraulic cyclone centrifuge, a hydrocyclone centrifuge, a horizontal spiral centrifuge, and any combination thereof.

In some embodiments, the method further comprises filtering the isolated long chain dicarboxylic acids. In some instances, the method further comprises drying the isolated long chain dicarboxylic acids.

The isolated long chain dicarboxylic acids can have a purity of at least 95% or higher. Alternatively, the long chain dicarboxylic acids have a purity of at least 97% or higher. In some cases, the long chain dicarboxylic acid is a saturated or unsaturated straight chain dicarboxylic acid having 9 to 18 carbon atoms, with a carboxyl group at two ends of the chain. In other cases, the long chain dicarboxylic acid is a saturated or unsaturated straight chain dicarboxylic acid having 11 to 14 carbon atoms, with a carboxyl group at each of the two ends of the chain. In some embodiments, the long chain dicarboxylic acid is selected from the group consisting of a nonanedioic acid, decanedioic acid, undecanedioic acid, dodecanedioic acid, tridecanedioic acid, tetradecanedioic acid, pentadecanedioic acid, hexadecanedioic acid, heptadecanedioic acid, octadecanedioic acid, 9-ene-octadecanedioic acid, and any combination thereof. In some instances, the long chain dicarboxylic acid is selected from the group consisting of an undecanedioic acid, dodecanedioic acid, tridecanedioic acid, tetradecanedioic acid, and any combination thereof.

In another aspect, described herein is a method for isolating a long chain dicarboxylic acid from a fermentation broth containing microbial cells. The method comprises: (a) adding sulfuric acid to the fermentation broth to produce a demulsified fermentation broth having a pH of 2.5-4; (b) heating the demulsified fermentation broth to a temperature from 90° C. to 105° C.; (c) centrifuging the demulsified fermentation broth to generate a first phase comprising the long chain dicarboxylic acid and a second phase comprising the microbial cells, wherein the first phase is substantially free of the microbial cells and the second phase is substantially free of the long chain dicarboxylic acid; and (d) isolating the long chain dicarboxylic acid from the first phase to recover an isolated long chain dicarboxylic acid.

In yet another aspect, provided herein is a method for isolating a long chain dicarboxylic acid from a fermentation broth containing microbial cells. The method comprises: (a) heating the demulsified fermentation broth to a temperature from 90° C. to 105° C.; (b) adding sulfuric acid to the fermentation broth to produce a demulsified fermentation broth having a pH of 2.5-4; (c) centrifuging the demulsified fermentation broth to generate a first phase comprising the long chain dicarboxylic acid and a second phase comprising the microbial cells, wherein the first phase is substantially free of the microbial cells and the second phase is substantially free of the long chain dicarboxylic acid; and (d) isolating the long chain dicarboxylic acid from the first phase to recover an isolated long chain dicarboxylic acid.

In some embodiments, the method for isolating a long chain dicarboxylic acid from a fermentation broth containing microbial cells comprises: (a) adding sulfuric acid to the fermentation broth to produce a demulsified fermentation broth having a pH of 2.5-4; (b) heating the demulsified fermentation broth to a temperature from 90° C. to 105° C.; (c) cooling the demulsified fermentation broth down to about 80° C. to about 30° C.; (d) centrifuging the demulsified fermentation broth to generate a first phase comprising the long chain dicarboxylic acid and a second phase comprising the microbial cells, wherein the first phase is substantially free of the microbial cells and the second phase is substantially free of the long chain dicarboxylic acid; and (e) isolating the long chain dicarboxylic acid from the first phase to recover an isolated long chain dicarboxylic acid.

In other embodiments, the method for isolating a long chain dicarboxylic acid from a fermentation broth containing microbial cells comprises: (a) heating the demulsified fermentation broth to a temperature from 90° C. to 105° C.; (b) cooling the demulsified fermentation broth down to about 80° C. to about 30° C.; (c) adding sulfuric acid to the fermentation broth to produce a demulsified fermentation broth having a pH of 2.5-4; (d) centrifuging the demulsified fermentation broth to generate a first phase comprising the long chain dicarboxylic acid and a second phase comprising the microbial cells, wherein the first phase is substantially free of the microbial cells and the second phase is substantially free of the long chain dicarboxylic acid; and (e) isolating the long chain dicarboxylic acid from the first phase to recover an isolated long chain dicarboxylic acid.

In yet another aspect, described herein is a substantially pure long chain dicarboxylic acid isolated according to any one of the methods provided herein.

In some embodiments, the substantially pure long chain dicarboxylic acid has a purity of at least 95% or more. In other embodiments, the substantially pure long chain dicarboxylic acid has a purity of at least 97% or more. The substantially pure long chain dicarboxylic acid can be a saturated or unsaturated straight chain dicarboxylic acid having 9 to 18 carbon atoms, with a carboxyl group at each of the two ends of the chain. Alternatively, the substantially pure long chain dicarboxylic acid can be a saturated or unsaturated straight chain dicarboxylic acid having 11 to 14 carbon atoms, with a carboxyl group at each of the two ends of the chain. In certain cases, the substantially pure long chain dicarboxylic acid is selected from the group consisting of an undecanedioic acid, dodecanedioic acid, tridecanedioic acid, tetradecanedioic acid, and any combination thereof.

Other objects, features, and advantages of the present invention will be apparent to one of skill in the art from the following detailed description and figures.

DETAILED DESCRIPTION OF THE INVENTION

I. Introduction

The invention provides an effective method for solid-solid separation to isolate long chain dicarboxylic acids from a fermentation broth. This invention provides a more efficient isolation or extraction process that includes heating the broth and directly adding an acid to precipitate the dibasic acid. At this step, the broth emulsion is broken, and precipitation of the dicarboxylic acid increases such that centrifugation can be used to separate cells from the dicarboxylic acid particles. The method is simple with fewer steps and requires less monetary investment. In addition, the consumption of acids and bases are greatly reduced compared to standard method. As such, fewer salts (typically $Na_2SO_4$) are found in the waste water, which reduces waste water treatment costs and minimizes the potential of environmental damage.

II. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "long chain dicarboxylic acid" refers to an α,ω-dicarboxylic acid. Non-limiting examples of long chain carboxylic acids include nonanedioic acids (azelaic acids), decanedioic acids, undecanedioic acids, dodecanedioic acids, tridecanedioicaicds (bras sylic acids), tetradecanedioic acids, pentadecanedioic acids, hexadecanedioic acids, heptadecanedioic acids, octadecanedioic acids, variants thereof, and derivatives thereof.

The term "mixture" refers to an aqueous liquid composition suitable for extraction by means described herein allowing the presence of some dicarboxylic acid, preferably more than 80%, more preferably than 95% by weight.

The term "fermentation broth", "fermentation stream", or "fermentation liquor" refers to an aqueous stream comprising one or more types of carboxylic acids that have been synthesized by a microbe (microorganism). Microorganisms that may be employed in the fermentation include wild-type or recombinant *Escherichia, Zymomonas, Candida, Pichia, Streptomyces, Bacillus, Lactobacillus* and *Clostridium*. In some embodiments, a fermentation broth includes one type of carboxylic acid. In other embodiments, a fermentation broth includes at least two types of carboxylic acids.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. For example, recombinant cells express genes that are not found within the native (non-recombinant) form of the cell or express native genes that are otherwise abnormally expressed, under-expressed, or not expressed at all.

The term "sterilized fermentation broth" refers to a fermentation broth that has been treated by heating to kill or inactivate the microbial cells present in the broth.

The term "demulsified", in the context of a fermentation broth, refers to a mixture that has been separated into some or all of its constituent components such that it is unable to reform the original mixture without aid.

The term "substantially free of" refers to a composition that is about 85%, 86%, 87%, 88%, 89%, 90%, 91%, 92%, 93%, 94%, 95%, 96%, 97%, 98%, or 99% or more free of undesired components.

The term "substantially pure" refers to a composition that is about 85%, 86%, 87%, 88%, 89%, 90%, 91%, 92%, 93%, 94%, 95%, 96%, 97%, 98%, or 99% or more pure.

The term "sequential centrifugation" refers to performing two or more centrifugations in succession without performing an intervening step other than moving the mixture or composition between centrifuges.

The term "isolated" or "separated" refers to a chemical compound, molecule, cell and the like that is separated from other components with which it is associated in a natural or unnatural state. The term does not mean that the preparation is technically pure (homogeneous), but rather that it is sufficiently pure to provide the chemical compound, molecule, cell and the like in a form in which it can be used for the intended purpose. In certain embodiments, the isolated composition comprising the dicarboxylic acid is at least about 95%, 96%, 97%, 98%, or 99% or more pure.

III. Detailed Descriptions of Embodiments

Provided herein is a method for isolating a long chain dicarboxylic acid from a fermentation broth containing microbial cells. The method includes (a) adding an acid to the fermentation broth to produce a demulsified fermentation broth having a pH of 6 or less; (b) centrifuging the demulsified fermentation broth to generate a first phase, e.g., a heavy phase, comprising the long chain dicarboxylic acid and a second phase, e.g., a light phase, comprising the microbial cells; and (c) isolating the long chain dicarboxylic acid from the first phase to recover an isolated long chain dicarboxylic acid.

In some embodiments, the fermentation broth includes microbial cells. In some cases, the fermentation broth is a diluted fermentation broth. The fermentation broth or diluted fermentation broth can include at least 0.5% microbial cells (dry weight), e.g., 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 3%, 4%, 5%, 6%, 7%, 8%, 9%, 10%, 11%, 12%, 13%, 14%, 15% or more microbial cells (dry weight). In some instances, the fermentation broth includes about 0.5% to about 10% microbial cells, e.g., about 0.5% to about 10%, about 0.5% to about 9%, about 0.5% to about 8%, about 0.5% to about 7%, about 0.5% to about 6%, about 0.5% to about 5%, about 0.5% to about 4%, about 0.5% to about 3%, about 0.5% to about 2%, about 0.5% to about 1%, about 1% to about 10%, about 1% to about 9%, about 1% to about 8%, about 1% to about 7%, about 1% to about 6%, about 1% to about 5%, about 1% to about 4%, about 1% to about 3%, about 1% to about 2%, about 0.5% to about 1%, about 1% to about 2%, about 2% to about 3%, about 3% to about 4%, about 4% to about 5%, about 5% to about 6%, about 6% to about 7%, about 7% to about 8%, about 8% to about 9%, about 9% to about 10%, or more microbial cells. In some embodiments, the fermentation broth contains 10% microbial cells. Non-limiting examples of microbial cells include *Escherichia, Zymomonas, Candida, Pichia, Streptomyces, Bacillus, Lactobacillus* and *Clostridium*. The microbial cells can be natural (wild-type) or recombinant. In some instances, the microbial cells of the fermentation broth are not removed via filtration or centrifugation.

In some instances, the concentration of all dicarboxylic acids in the fermentation broth is at least about 85% (dry weight), e.g., about 85%, about 86%, about 87%, about 88%, about 89%, about 90%, about 91%, about 92%, about 93%, about 94%, about 95%, or more (dry weight). The total concentration of dicarboxylic acids in the fermentation broth can be at least about 90% (dry weight).

In some embodiments, the first phase, e.g., the heavy phase, is substantially free of the microbial cells. The first phase or heavy phase can include less than 0.5% (w/w)

microbial cells, e.g., 0.4% (w/w), 0.3% (w/w), 0.2% (w/w), 0.1% (w/w) or no microbial cells. The first phase or heavy phase can contain about 0% to about 0.4% (w/w), e.g., about 0% (w/w) to about 0.4% (w/w), about 0% to about 0.3% (w/w), about 0% (w/w) to about 0.2% (w/w), about 0% (w/w) to about 0.1% (w/w), about 0.1% (w/w) to about 0.4% (w/w), about 0.1% (w/w) to about 0.3% (w/w), about 0.1% (w/w) to about 0.2% (w/w), about 0.2% (w/w) to about 0.4% (w/w) or about 0.2% (w/w) to about 0.3% (w/w) microbial cells. In some cases, the first phase or heavy phase is free of microbial cells. In some instances, at least 80% (w/w), e.g., 80% (w/w), 81% (w/w), 82% (w/w), 83% (w/w), 84% (w/w), 85% (w/w), 86% (w/w), 87% (w/w), 88% (w/w), 89% (w/w), 90% (w/w), 91% (w/w), 92% (w/w), 93% (w/w), 94% (w/w), 95% (w/w), 96% (w/w), 97% (w/w), 98% (w/w), 99% (w/w), or more of the microbial cells of the fermentation broth or the demulsified fermentation broth are present in the second phase or light phase.

The method described herein can remove at least about 80%, e.g., about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% of the microbial cells in the fermentation broth. In some cases, about 80%-about 90%, about 80%-about 99%, about 85%-about 90%, about 80%-about 95%, about 85%-about 95%, about 85%-about 99%, about 90%-about 95%, or about 95%-about 99% of the cells can be removed from the fermentation broth.

In some embodiments, the first phase, e.g., heavy phase, contains about 10% (w/w) to about 80% (w/w) long chain dicarboxylic acid, e.g., about 10% (w/w) to about 80% (w/w), about 20% (w/w) to about 80% (w/w), about 30% (w/w) to about 80% (w/w), about 40% (w/w) to about 80% (w/w), about 50% (w/w) to about 80% (w/w), about 60% (w/w) to about 80% (w/w), about 10% (w/w) to about 60% (w/w), about 10% (w/w) to about 40% (w/w), about 40% (w/w) to about 80% (w/w), about 20% (w/w) to about 60% (w/w), about 40% (w/w) to about 60% (w/w), about 10% (w/w), about 20% (w/w), about 30% (w/w), about 40% (w/w), about 50% (w/w), about 60% (w/w), about 70% (w/w), or about 80% (w/w) long chain dicarboxylic acid. In some instances, at least 80% (w/w), e.g., 80% (w/w), 81% (w/w), 82% (w/w), 83% (w/w), 84% (w/w), 85% (w/w), 86% (w/w), 87% (w/w), 88% (w/w), 89% (w/w), 90% (w/w), 91% (w/w), 92% (w/w), 93% (w/w), 94% (w/w), 95% (w/w), 96% (w/w), 97% (w/w), 98% (w/w), 99% (w/w) or more of the long chain dicarboxylic acid in the fermentation broth or the demulsified fermentation broth is present in the first phase or heavy phase. The concentration or amount of long chain dicarboxylic acid can be determined by, for example, gas chromatography.

In some embodiments, the second phase, e.g., the light phase, is substantially free of long chain dicarboxylic acid. This phase can include less than 10% (w/w) long chain dicarboxylic acid, e.g., 9.8% (w/w), 9.5% (w/w), 9.0% (w/w), 8.5% (w/w), 8.0% (w/w), 7.5% (w/w), 7.0% (w/w), 6.5% (w/w), 6.0% (w/w), 5.5% (w/w), 5.0% (w/w), 4.5%, 4.0% (w/w), 3.5% (w/w), 3.0% (w/w), 2.5% (w/w), 2.0% (w/w), 1.5% (w/w), 1.0% (w/w), 0.5% (w/w), or less long chain dicarboxylic acid. In some cases, the second phase or light phase is free of long chain dicarboxylic acid.

The fermentation broth can be a sterilized fermentation broth. In some embodiments, a fermentation broth is heated to about 90° C. to about 105° C., e.g., about 90° C. to about 105° C., about 90° C. to about 102° C., about 90° C. to about 100° C., about 90° C. to about 98° C., about 90° C. to about 96° C., about 90° C. to about 94° C., about 90° C. to about 92° C., about 91° C. to about 105° C., about 93° C. to about 105° C., about 95° C. to about 105° C., about 97° C. to about 105° C., about 99° C. to about 105° C., about 100° C. to about 105° C., about 90° C., about 91° C., about 92° C., about 93° C., about 94° C., about 95° C., about 96° C., about 97° C., about 98° C., about 99° C., about 100° C., about 101° C., about 102° C., about 103° C., about 104° C., or about 105° C. prior to adding the acid in step (a) of the method described herein. In other embodiments, a fermentation broth is heated to about 90° C. to about 105° C., e.g., about 90° C. to about 105° C., about 90° C. to about 102° C., about 90° C. to about 100° C., about 90° C. to about 98° C., about 90° C. to about 96° C., about 90° C. to about 94° C., about 90° C. to about 92° C., about 91° C. to about 105° C., about 93° C. to about 105° C., about 95° C. to about 105° C., about 97° C. to about 105° C., about 99° C. to about 105° C., about 100° C. to about 105° C., about 90° C., about 91° C., about 92° C., about 93° C., about 94° C., about 95° C., about 96° C., about 97° C., about 98° C., about 99° C., about 100° C., about 101° C., about 102° C., about 103° C., about 104° C., or about 105° C. prior to centrifuging the demulsified fermentation broth in step (b) of the method described herein.

In some embodiments, the sterilized fermentation broth is cooled to a temperature ranging from about 80° C. to about 30° C., e.g., about 80° C. to about 30° C., about 75° C. to about 30° C., about 70° C. to about 30° C., about 65° C. to about 30° C., about 60° C. to about 30° C., about 55° C. to about 30° C., about 50° C. to about 30° C., about 45° C. to about 30° C., about 40° C. to about 30° C., about 80° C. to about 40° C., about 80° C. to about 50° C., about 80° C. to about 60° C., about 80° C. to about 70° C., about 80° C., about 70° C., about 60° C., about 50° C., about 40° C., about 30° C., and the like, prior to heating to the demulsified fermentation broth in step (a) or step (b) of the method described herein.

To generate a demulsified fermentation broth having a pH of 6.0 or less, e.g., pH 6.0, pH 5.9, pH 5.8, pH 5.7, pH 5.6, pH 5.5, pH 5.4, pH 5.3, pH 5.2, pH 5.1, pH 5.0, pH 4.9, pH 4.8, pH 4.7, pH 4.6, pH 4.5, pH 4.4, pH 4.3, pH 4.2, pH 4.1, pH 4.0, pH 3.9, pH 3.8, pH 3.7, pH 3.6, pH 3.5, pH 3.4, pH 3.3, pH 3.2, pH 3.1, pH 3.0, pH 2.9, pH 2.8, pH 2.7, pH 2.6, pH 2.5, pH 2.4, pH 2.3, pH 2.2, pH 2.1, pH 2.0 or less, an acid can be added to the fermentation broth. Useful acids include, but are not limited to, sulfuric acid, hydrochloric acid, nitric acid, acetic acid, phosphoric acid, trifluoromethane sulfonic acid, and any combination thereof. In some embodiments, the acid is sulfuric acid. In some embodiments, the demulsified fermentation broth has a pH ranging from pH 2 to pH 5, e.g., pH 2 to pH 5, pH 2.5 to pH 5, pH 3 to pH 5, pH 3.5 to pH 5, pH 4 to pH 5, pH 2.5 to pH 4.5, pH 2.5 to pH 4, pH 2.5 to pH 3.5, and the like. The demulsified fermentation broth has a pH ranging from pH 2.5 to pH 4.

The acid for generating a demulsified fermentation broth can be 2.5M-5M acid, e.g., 2.5M-5M, 2.5M-4M, 3M-5M, 3M-4M, 2.5M-4M, 2.5-3.5M, 3.5M-4.5M, 4M-5M, 2.5M-3M, 3M-3.5M, 3.5M-4M, 4M-4.5M, 4.5M-5M, 2.5M, 3M, 3.5M, 4M, 4.5M, or 5M, and the like. In some embodiments, 2.5M-5M sulfuric acid, e.g., 2.5M-5M, 2.5M-4M, 3M-5M, 3M-4M, 2.5M-4M, 2.5-3.5M, 3.5M-4.5M, 4M-5M, 2.5M-3M, 3M-3.5M, 3.5M-4M, 4M-4.5M, 4.5M-5M, 2.5M, 3M, 3.5M, 4M, 4.5M, or 5M hydrochloric acid is added to the fermentation broth. In certain embodiments, 2.5M-5M sulfuric acid, e.g., 2.5M-5M, 2.5M-4M, 3M-5M, 3M-4M, 2.5M-4M, 2.5-3.5M, 3.5M-4.5M, 4M-5M, 2.5M-3M, 3M-3.5M, 3.5M-4M, 4M-4.5M, 4.5M-5M, 2.5M, 3M, 3.5M, 4M, 4.5M, or 5M hydrochloric acid is added to the fermentation broth. In other embodiments, 2.5M-5M acetic acid, phosphoric acid, nitric acid, or trifluoromethane sulfonic acid, e.g., 2.5M-5M, 2.5M-4M, 3M-5M, 3M-4M, 2.5M-4M, 2.5-3.5M, 3.5M-4.5M, 4M-5M, 2.5M-3M, 3M-3.5M, 3.5M-4M, 4M-4.5M, 4.5M-5M, 2.5M, 3M, 3.5M, 4M, 4.5M, or 5M acetic acid, phosphoric acid, nitric acid, or trifluoromethane sulfonic acid is added to the fermentation broth. In some cases, 10%-20% (v/v) sulfuric acid, e.g., 10%-20% (v/v), 11%-20% (v/v), 10%-15% (v/v), 15%-20% (v/v), 11%-15% (v/v), 10% (v/v), 11% (v/v), 12% (v/v), 13% (v/v), 14% (v/v), 15% (v/v), 16% (v/v), 17% (v/v), 18% (v/v), 19% (v/v), or 20% (v/v) sulfuric acid is added to the fermentation broth.

In some embodiments, the demulsified fermentation broth has a viscosity of about 5 centipoise (cp) to about 200 cp, e.g., about 5 cp to about 200 cp, about 50 cp to about 200 cp, about 100 cp to about 200 cp, about 150 cp to about 200 cp, about 5 cp to about 150 cp, about 5 cp to about 100 cp, about 5 cp to about 50 cp, about 5 cp, about 10 cp, about 20 cp, about 30 cp, about 40 cp, about 50 cp, about 60 cp, about 70 cp, about 80 cp, about 90 cp, about 100 cp, about 110 cp, about 120 cp, about 130 cp, about 140 cp, about 150 cp, about 160 cp, about 170 cp, about 180 cp, about 190 cp, or about 200 cp. Viscosity can be measured using, for example, a viscosimeter.

In some embodiments, the first phase (e.g., the heavy phase) and the second phase (e.g., the light phase) are produced from the demulsified fermentation broth by centrifugation. Centrifugation can be performed via sequential centrifugation. In some instances, centrifuging is performed using a scanter centrifuge, such as but not limited to, a hydraulic cyclone centrifuge, a hydrocyclone centrifuge, a horizontal spiral centrifuge, and any combination thereof.

In some embodiments, the long chain dicarboxylic acid is a long chain dicarboxylic acid solid or particle. The long chain dicarboxylic acid of the first phase or heavy phase can be isolated or recovered using, for example, any solid-liquid separation method known by one of ordinary skill in the art. The isolated long chain dicarboxylic acid can have a purity of at least 95% or higher, e.g., 95%, 96%, 97%, 98%, 99%, 99.5% or more. For instance, the isolated long chain dicarboxylic acid can be about 97%, 98%, 99%, 99.5% or more pure.

In some embodiments, the isolated long chain dicarboxylic acid is filtered using, for example, plate frame filtration. In some instances, the isolated long chain dicarboxylic acid is dried. The long chain dicarboxylic acid can be further processed into a crystal form. The isolated long chain dicarboxylic acid can be filtered, dried, and then heated to about 90° C. or any other temperature to dissolve the dicarboxylic acid. In some instances, an activated carbon can be added and maintained at about 90° C. or higher for about 30 minutes to about 2 hours. In some cases, the temperature of the dicarboxylic acid mixture containing activated carbon is kept at 90° C. for 1 hour. Afterwards, the mixture can be filtered to produce a decolorized solution that includes the dicarboxylic acid. The decolorized solution can be cooled to about 28° C. The crystal form of the dicarboxylic acid can be separated from the decolorized solution by, e.g., centrifugation. The dicarboxylic acid crystal can be washed, and optionally, dried. The dried dicarboxylic acid crystal can also be chipped.

In another aspect, described herein is a method for isolating a long chain dicarboxylic acid from a fermentation broth containing microbial cells comprising (a) adding sulfuric acid to the fermentation broth to produce a demulsified fermentation broth having a pH of 2.5-4; (b) heating the demulsified fermentation broth to a temperature from 90° C. to 100° C.; (c) centrifuging the demulsified fermentation broth to generate a first phase comprising the long chain dicarboxylic acid and a second phase comprising the microbial cells, wherein the first phase is substantially free of the microbial cells and the second phase is substantially free of the long chain dicarboxylic acid; (d) isolating the long chain dicarboxylic acid from the first phase to recover an isolated long chain dicarboxylic acid.

In yet another aspect, described herein is a substantially pure long chain dicarboxylic acid isolated according to any one of the methods provided herein. In other words, the long chain dicarboxylic acid is about 95%, 96%, 97%, 98%, 99% or more pure. In some embodiments, the isolated and substantially pure long chain dicarboxylic acid is 95%, 96%, 97%, 98%, 99% or more pure. In other embodiments, the isolated dicarboxylic acid is 100% pure.

The method provided herein can be used to separate, isolate, extract, or recover long chain dicarboxylic acids from a fermentation broth or other aqueous mixtures (e.g., fermentation streams). The fermentation broth can contain one or more microbial cells that can synthesize long chain dicarboxylic acids and nutrients such as sugar to maintain the growth of the cells.

In some instances, drying includes dewatering the recovered long chain dicarboxylic acids to reduce the amount or level of water present. The dried long chain dicarboxylic acids can contain less than 5% water, e.g., 4.5%, 4%, 3.5%, 3%, 2.5%, 2%, 1.5%, 1%, 0.9%, 0.8%, 0.7%, 0.6%, 0.5%, 0.4%, 0.3%, 0.2%, 0.1% or less by w/w or v/v. Water content can be determined by using volumetric and coulometric Karl Fischer titration methods which are recognized by those of skill in the art.

In some embodiments, the isolated long chain dicarboxylic acid comprises a solid precipitate or particle of the dicarboxylic acid. In some embodiments, the average size of the particle (e.g., the mean volume of the particle) of the long chain dicarboxylic acids ranges from about 0.1 μm to about 2000 μm, e.g., about 0.1 μm to about 2000 μm, about 0.1 μm to about 1000 μm, about 0.1 μm to about 500 μm, about 0.1 μm to about 100 μm, about 1 μm to about 2000 μm, about 1 μm to about 1000 μm, about 1 μm to about 500 μm, about 1 μm to about 100 μm, about 10 μm to about 2000 μm, about 10 μm to about 1000 μm, about 10 μm to about 500 μm, about 10 μm to about 400 μm, about 10 μm to about 300 μm, about 10 μm to about 200 μm, about 10 μm to about 100 μm, about 10 μm to about 500 μm, about 20 μm to about 500 μm, about 30 μm to about 500 μm, about 40 μm to about 500 μm, about 50 μm to about 500 μm, about 60 μm to about 500 μm, about 70 μm to about 500 μm, about 80 μm to about 500 μm, about 90 μm to about 500 μm, about 100 μm to about 500 μm, about 10 μm to about 90 μm, about 10 μm to about 80 μm, about 10 μm to about 70 μm, about 10 μm to about 60 μm, about 10 μm to about 50 μm, about 10 μm to about 40 μm, about 10 μm to about 30 μm, about 20 μm to about 100 μm, about 30 μm to about 100 μm, about 40 μm to about 100 μm, about 50 μm to about 100 μm, about 60 μm to about 100 μm, about 70 μm to about 100 μm, about 80 μm to about 100 μm, about 90 μm to about 100 μm, and the like. In certain cases, the average size of the particle is greater than 10 μm, e.g., 11 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 150 μm, 200 μm, 250 μm, 300 μm, 350 μm, 400 μm, 450 μm, 500 μm, 550 μm, 600 μm, 650 μm, or more.

The substantially pure or pure dicarboxylic acid can be further processed. In some instances, the dicarboxylic acid is dried. In other instances, the substantially pure or pure dicarboxylic acid is filtered, e.g., plate frame filtered. In certain instances, the dicarboxylic acid is filtered, dried, treated with an acid, heated, centrifuged, washed, chipped, or any combination thereof. For instance, the precipitated dicarboxylic acid can be (1) filtered (e.g., plate frame filtered) and dried, (2) treated or contacted with an acid (e.g., acetic acid), (3) heated to about 90° C. to dissolve the dicarboxylic acid, (4) contacted with an activated carbon, (5) heated to about 90° C. to produce a decolorized solution, and (6) cooled to about 28° C. to form dicarboxylic acid crystals. In some embodiments, the dicarboxylic acid crystals are washed, dried and chipped.

The long chain dicarboxylic acid of the present disclosure can be a saturated or unsaturated straight chain dicarboxylic acid having 9 to 18 carbon atoms, with a carboxyl group at each of the two ends of the chain. In other embodiments, the long chain dicarboxylic acid is a saturated or unsaturated straight chain dicarboxylic acid having 11 to 14 carbon atoms, with a carboxyl group at each of the two ends of the chain. The long chain dicarboxylic acid can be selected from the group consisting of an undecanedioic acid, dodecanedioic acid, tridecanedioic acid (brassylic acid), tetradecanedioic acid, pentadecanedioic acid, hexadecanedioic acid, and any combination thereof. In some instances, the long chain dicarboxylic acid is an undecanedioic acid, dodecanedioic acid, tridecanedioic acid (brassylic acid), tetradecanedioic acid, or any combination thereof.

IV. Examples

The following examples are offered to illustrate, but not to limit, the claimed invention.

Example 1. Isolation of Dodecanedioic Acid (DC12) from a Fermentation Broth 5 m$^3$ of the fermentation broth of dodecanedioic acid (DC12, produced by Shandong Cathay Biomaterials Ltd.) was obtained. The broth contained 12% dodecanedioic acid and 1.2% cells. The fermentation broth was heated to 90° C. The heated broth was stirred while a sulfuric acid solution (3 mol/L) was added into the fermentation broth. The pH value of the mixture was adjusted to 4.5. The temperature was kept at 95° C.–100° C. for 30-60 min during the acidification. The demulsified mixture was slowly cool down to 60° C., and then centrifuged using, for example, a three-series cyclone system (RWT 1530) at a feed rate of 16 m$^3$/h and a feed pressure of 5-6 kg. Two outflows from the centrifuge were used: one for the heavy phase which contained most of the dibasic acid particles and the other for the light phase which contained most of the microbial cells and water. The contents of the light phase were directly flowed to waste water treatment station.

The concentration of all diacids in the fermentation broth was about 90% (according to dry weight analysis) and the concentration of the cells was about 10% (by dry weight). The yield of DC12 by the method described herein was 98%. The removal rate of the total cells was 88.9%. The long chain diacid particles were collected through plate frame filtration. The purity of isolated DC12 products was 97.2%, as determined by gas chromatography (GC).

The following method to determine the concentration of cells in the fermentation broth was used in Examples 1 to 5 described herein. About 100 g of the sample fermentation broth was weighted to an accuracy of two decimal places and recorded as "M1". A 30% NaOH (% by weight) solution was added to the sample and heated to completely dissolve the long chain dicarboxylic acids and raise the pH to pH 9.5. The mixture was cooled down to room temperature, and centrifuged at about 4000 rpm for about 10 minutes using, for example, a 250 mL centrifuging cup in order to pellet the microbial cells. The supernatant fluid was decanted and about 100 mL ionized water was added and stirred. The centrifugation step was repeated, and the supernatant fluid was again decanted. The pelleted cells were dried at 100° C. to a constant weight. The weight was recorded of the dried pellet as "M2" (to an accuracy of two decimal places). The concentration of the cells in the fermentation broth was calculated using the formula: C=(M2×100%)/M1.

The total removal rate of the cells was determined by measuring the concentration of cells of the fermentation broth before treatment (C1) and after isolation of the long chain dicarboxylic acids (C2). The total removal rate of cells was calculated using the formula: ((C1-C2)×100%)/C1.

The yield of the long chain dicarboxylic acid from the isolation method was calculated using the formula: yield= ((V2×C2)×100%)/(V1×C1), wherein C1 represents the concentration of long chain dicarboxylic acid in the fermentation broth; V1 represents the volume of fermentation broth treated using the method described herein; C2 represents the concentration of long chain dicarboxylic acid in the heavy phase (first phase), and V2 represents the volume of the heavy phase (first phase).

Example 2. Isolation of Dodecanedioic Acid (DC12) from a Fermentation Broth 5 m$^3$ of the fermentation broth of dodecanedioic acid (DC12, produced by Shandong Cathay Biomaterials Ltd.) was obtained, of which the concentration of dodecanedioic acid was 12% and the concentration of the cells was 1.2%. The fermentation broth was stirred while a sulfuric acid solution (3 mol/L) was added into the broth. The pH value of the mixture was adjusted to 5.5. Then the mixture was heated to 98° C. and maintained at this temperature for 20 min. The mixture was then slowly cooled down to 35° C. Next, the mixture was centrifuged using, for example, a horizontal spiral centrifuge (Model 250) at a centrifugal force of 3000-3100 g and a feed rate of 3.6 m$^3$/h. There were two outflow phases from the centrifuge. One was used for the heavy phase which contains most of the dibasic acid particles, and the other was for the light phase which contains most of the cells and water. The light phase was directed to a waste water treatment station.

The concentration of all diacid particles in the broth (according to dry weight analysis) was about 90% and the concentration of the cells was about 10% (by dry weight). The yield of DC12 by the method was 98.5%. The total removal rate of the cells was 90.7%. The power consumption of the centrifuge was 50 kwh per ton of DC12.

The long chain diacid particles were collected through plate frame filtration. The purity of products was 95% or higher, as determined by gas chromatography (GC). The long chain diacid particles can be used directly in the perfume industry. The power consumption of the whole process was 73 kwh per ton of DC12.

Example 3. Isolation of Tetradecanedioic Acid (DC14) from a Fermentation Broth 5 m$^3$ of the fermentation broth of tetradecanedioic acid (DC14, produced by Shandong Cathay Biomaterials Ltd.)

was obtained, of which the concentration of tetradecanedioic acid was 15% and the concentration of the cells was 1.4%. The fermentation broth was stirred as sulfuric acid solution (3 mol/L) was added into the broth. The pH value of the mixture was adjusted to 4. The fermentation broth was heated to 100° C. and kept at this temperature for 20 min. The demulsified broth was slowly cooled down to 30° C. The broth was then centrifuged using a horizontal spiral centrifuge (Model 250) at a centrifugal force of 2600 g and a feed rate of 5.2 m$^3$/h. Two outflow phases from the centrifuge were used: (1) a heavy phase that included most of dibasic acid particles and (2) a light phase that included most of cells and water. The low phase was directed to a waste water treatment station.

The concentration of all diacids in the fermentation broth (according to dry weight analysis) was about 90% and the concentration of the cells was about 10% (by dry weight). Using the method described herein the yield of DC14 was 98.2%. The removal rate of the total cells was 90%.

The obtained long chain diacid solution was filtered by plate frame and then dried to obtain a dry product. The purity for the isolated DC14 product was 97.5%, as determined by gas chromatography (GC).

100 kg of the dry long chain diacid product was mixed with 300 kg of 98% acetic acid. The mixture was then heated to 90° C. to dissolve the isolated DC14 product, thereafter activated carbon was added into the mixed solution. The mixed solution was kept at 90° C. for 1 hour, and then filtered to obtain a decolorized DC14 solution. The decolorized solution was slowly cooled down to 28° C. The crystalline form was separated from the decolorized solution by centrifugation at 1000 rpm. The crystalline DC14 was successively washed using 100 kg of acetic acid at room temperature and 200 kg of pure water, and then centrifuged. The DC14 product was dried and chipped to obtain a purified, solid DC14 product.

Example 4. Isolation of Tridecanedioic Acid (DC13) from a Fermentation Broth 5 m$^3$ of the fermentation broth of tridecanedioic acid (DC13, produced by Shandong Cathay Biomaterials Ltd.) was obtained. The broth contained 12% tridecanedioic acid and 0.96% cells. The concentration of tridecanedioic acid in the broth was diluted to 9%. The fermentation broth was stirred as sulfuric acid solution (3 mol/L) was added into the broth. As such, the pH of the mixture was adjusted to pH 5.5. The fermentation broth was heated to 95° C. and kept at this temperature for 80 min. The demulsified broth was slowly cooled down to 30° C. The resulting broth was centrifuged using, for example, a horizontal spiral centrifuge (Model 250) at a feed rate of 16 m$^3$/h. Two outflow phases were used from the centrifuge: a heavy phase that contained most of the tridecanedioic acid particles and a light phase that contained most of the microbial cells and water. The light phase was directed to a waste water treatment station.

The concentration of DC13 in the heavy phase was 95% (according to dry weight analysis). The yield of DC13 by the method described herein was 97.1%. The removal rate of the total cells was 88.0%. The power consumption of centrifuge was 55 kwh per ton of DC13.

Long chain DC13 particles were recovered after filtration and drying. The purity of the isolated DC13 product was 98%, as determined by gas chromatography (GC). These products can be used directly in fragrances and the like. The power consumption of the whole process was 70 kwh per ton of DC13. The use of centrifugation instead of membrane filtration to separate the desired long chain dicarboxylic acid provides a higher yield and higher purity compared to conventional or standard methods.

Example 5. Conventional, Prior Art Method for Isolating Dodecanedioic Acid (DC12) from a Fermentation Broth 10 m$^3$ of the fermentation broth was obtained. The fermentation broth contained about 12% DC12, and about 1.6% microbial cells. NaOH solution (30% wt) was added to the fermentation broth to raise the pH to pH 9.5. The mixture was heated to 90° C., and then filtered using a membrane filtration system to remove the cells and obtain a clear broth. The power consumption was 320 kwh per ton of DC12.

The clear broth was acidified with a sulfuric acid solution until the pH reached pH 4.5. The acidification process was performed at 95° C.-100° C. for 30-60 min. The resulting mixture was cooled slowly to 60° C., and then to 25° C.-30° C. quickly. The resulting mixture was filtered using a plate frame and dried to obtain an isolated DC12 product. The yield of the long-chain diacid (the isolated DC12 product) was 97%. The power consumption of the whole process was 370 kwh per ton of DC12. The consumption of 30% NaOH was 0.04 kg/kg of DC12.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for isolating a long chain dicarboxylic acid from a fermentation broth containing microbial cells, the method comprising:
   (a) adding an acid to the fermentation broth to produce a demulsified fermentation broth having a pH of 6 or less;
   (b) centrifuging the demulsified fermentation broth using a hydraulic cyclone centrifuge, a hydrocyclone centrifuge, a horizontal spiral centrifuge, or any combination thereof to generate a first phase comprising the long chain dicarboxylic acid and a second phase comprising the microbial cells; and
   (c) isolating the long chain dicarboxylic acid from the first phase by filtration to recover an isolated long chain dicarboxylic acid product.

2. The method of claim 1, wherein the first phase is substantially free of the microbial cells.

3. The method of claim 1 or 2, wherein the second phase is substantially free of the long chain dicarboxylic acid.

4. The method of claim 1 or 2, wherein the fermentation broth is a sterilized fermentation broth.

5. The method of claim 1 or 2, further comprising heating the fermentation broth to a temperature from about 90° C. to about 105° C. prior to step (a).

6. The method of claim 1 or 2, further comprising heating the demulsified fermentation broth to a temperature from about 90° C. to about 105° C. prior to step (b).

7. The method of claim 5, further comprising cooling the demulsified fermentation broth to a temperature from about 30° C. to about 80° C. after heating.

8. The method of claim 1 or 2, wherein the acid is selected from the group consisting of sulfuric acid, hydrochloric acid, nitric acid, acetic acid, phosphoric acid, trifluoromethane sulfonic acid, and any combination thereof.

9. The method of claim 1 or 2, wherein the acid is sulfuric acid.

10. The method of claim 1 or 2, wherein the demulsified fermentation broth has a pH of 2-5.

11. The method of claim 10, wherein the pH is pH 2.5-4.

12. The method of claim 1 or 2, wherein the demulsified fermentation broth has a viscosity of about 5 centipoise (cp)-about 200 cp.

13. The method of claim 1 or 2, wherein centrifuging comprises sequential centrifugation.

14. The method of claim 1 or 2, further comprising drying the isolated long chain dicarboxylic acid.

15. The method of claim 1 or 2, wherein the isolated long chain dicarboxylic acid has a purity of at least 95% or higher.

16. The method of claim 15, wherein the isolated long chain dicarboxylic acid has a purity of at least 97% or higher.

17. The method of claim 1 or 2, wherein the long chain dicarboxylic acid is a saturated or unsaturated straight chain dicarboxylic acid having 9 to 18 carbon atoms, with a carboxyl group at each of the two ends of the chain.

18. The method of claim 17, wherein the long chain dicarboxylic acid is a saturated or unsaturated straight chain dicarboxylic acid having 11 to 14 carbon atoms, with a carboxyl group at each of the two ends of the chain.

19. The method of claim 17, wherein the long chain dicarboxylic acid is selected from the group consisting of a nonanedioic acid, decanedioic acid, undecanedioic acid, dodecanedioic acid, tridecanedioic acid, tetradecanedioic acid, pentadecanedioic acid, hexadecanedioic acid, heptadecanedioic acid, octadecanedioic acid, 9-ene-octadecanedioic acid, and any combination thereof.

20. The method of claim 19, wherein the long chain dicarboxylic acid is selected from the group consisting of an undecanedioic acid, dodecanedioic acid, tridecanedioic acid, tetradecanedioic acid, and any combination thereof.

21. A method for isolating a long chain dicarboxylic acid from a fermentation broth containing microbial cells, the method comprising:
   (a) adding sulfuric acid to the fermentation broth to produce a demulsified fermentation broth having a pH of 2.5-4;
   (b) heating the demulsified fermentation broth to a temperature from 90° C. to 105° C.;
   (c) centrifuging the demulsified fermentation broth using a hydraulic cyclone centrifuge, a hydrocyclone centrifuge, a horizontal spiral centrifuge, or any combination thereof to generate a first phase comprising the long chain dicarboxylic acid and a second phase comprising the microbial cells, wherein the first phase is substantially free of the microbial cells and the second phase is substantially free of the long chain dicarboxylic acid; and
   (d) isolating the long chain dicarboxylic acid from the first phase by filtration to recover an isolated long chain dicarboxylic acid.

22. The method of claim 6, further comprising cooling the demulsified fermentation broth to a temperature from about 30° C. to about 80° C. after heating.

* * * * *